United States Patent [19]

Ziggiotti et al.

[11] Patent Number: 4,948,805

[45] Date of Patent: Aug. 14, 1990

[54] SALT OF DICLOFENAC WITH A PYRROLIDINE COMPOUND AND PHARMACEUTICAL COMPOSITIONS WHICH CONTAIN IT

[75] Inventors: Antonio Ziggiotti, Vezia, Switzerland; Michele Di Schiena, Cisliano, Italy

[73] Assignee: Altergon S. A. & Ricerfarma Srl., Italy

[21] Appl. No.: 117,823

[22] Filed: Nov. 9, 1987

[30] Foreign Application Priority Data

Nov. 13, 1986 [IT] Italy ................................ 22320 A/86

[51] Int. Cl.$^5$ ............................................. A61K 31/40
[52] U.S. Cl. ...................................... 514/428; 548/574
[58] Field of Search ................ 548/570, 574; 546/248; 540/609; 514/428, 315, 212

[56] References Cited

U.S. PATENT DOCUMENTS 3,558,690  1/1971  Sallmann ............................. 548/485

OTHER PUBLICATIONS

Chemical Abstracts, vol. 102, no. 26, Jul. 1, 1985, p. 336, Abstract no. 225919f.

*Primary Examiner*—John M. Ford
*Assistant Examiner*—Zinna Northington-Davis
*Attorney, Agent, or Firm*—Arnold, White & Durkee

[57] ABSTRACT

The salt of diclofenac with a cyclic organic base is prepared by dissolving diclofenac in a suitable organic solvent, adding said cyclic organic base, reacting the two components together, removing the solvent and crystallizing the product obtained.

Said salt is water soluble to an extent from 20% w/v to an extent exceeding 50% w/v, and is used to prepared pharmaceutical compositions preferably in granular form for use by dissolving in water for oral administration.

4 Claims, No Drawings

SALT OF DICLOFENAC WITH A PYRROLIDINE COMPOUND AND PHARMACEUTICAL COMPOSITIONS WHICH CONTAIN IT

DESCRIPTION OF THE TECHNICAL FIELD

This invention relates to the salt of diclofenac with a cyclic organic base and to pharmaceutical compositions which contain it.

More particularly, the invention relates to the salt of diclofenac with a cyclic organic base in the various pharmaceutical forms, and preferably in granular form for use in extemporaneous solutions for oral administration.

Diclofenac (2[2,6-dichlorophenyl)-amino]benzeneacetic acid) is an anti-inflammatory medicament which has been known for a considerable time and which together with numerous other compounds falls under the general formula of U.S. Pat. No. 3,558,690.

One of the characteristics of these compounds is that they cyclize in an acid environment to give the corresponding indolinones. In order to obtain stabilization of the open form, they are salified with non-toxic organic or inorganic bases as described for example in the aforesaid patent. However, in this patent no information is given regarding the solubility of said salts in water, and notwithstanding the fact that several years have passed since the teachings of the said patent were made available, no aqueous pharmaceutical composition of diclofenac has been marketed.

BRIEF SUMMARY OF THE INVENTION

We have now found that it is possible to obtain a highly water soluble diclofenac salt by salifying diclofenac with a cyclic organic base having the general formula (I)

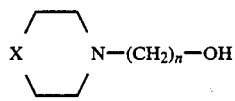

in which X is a group of the formula $(CH_2)_m$, in which m is 0 or 1 or 2, or X is oxygen or S or NR, in which R is an alkyl group $C_1$-$C_4$, and n is 2 or 3. This is very surprising in the light of the fact that U.S. Pat. No. 3,558,690 comprises salts of diclofenac with bases such as 2-aminoethanol and pyrrolidine which are very close to the bases of the formula (I) from a structural viewpoint, whereas these salts are practically insoluble in water.

In contrast to the tablet form currently used for oral administration one particular unforseeable advantage of the salt of diclofenac with a base of formula (I) is that when prepared in granular form and stored in water-impermeable sachets, it enables extemporaneous aqueous solutions to be prepared which while totally maintaining their activity level do not give rise to gastrolesion.

The enormous advantage of such a behaviour which obviates any risk to the patient ingesting the medicament is an obvious considerable merit in terms of its pharmaceutical application.

The salt of diclofenac with a base of formula (1) therefore constitutes a subject of the present invention, a further subject of the invention being pharmaceutical compositions containing a therapeutically useful dosage of said salt.

The process for preparing this salt is extremely simple from an industrial viewpoint, it being characterized by dissolving diclofenac in a suitable organic solvent, adding a base of formula (I), reacting said compounds together at ambient temperature, removing the solvent and crystallising the product obtained.

DETAILED DESCRIPTION OF THE PREFERRED EMBODIMENTS

Suitable organic solvents for dissolving diclofenac are acetone, ethanol and chloroform. The base used in equimolar quantity or in slight excess with respect to the diclofenac. The reaction is conducted at ambient temperature under agitation for a time of between 0.5 and 3 hours. The solvent is removed by distillation under vacuum at a temperature of between 35° and 45° C. The salt is crystallised by treating the distillation residue with hexane or petroleum ether under energetic agitation. The unrefined salt obtained is redissolved in acetone and recrystallised from hexane or petroleum ether.

The solubility characteristics of the salt of diclofenac with hydroxy-ethylpyrrolidine (ID) and with hydroxyethylpiperidine (IP) compared with the salts of diclofenac with sodium (SD), with pyrrolidine (PD) and with 2-aminoethanol (AD) are given in the following table.

| Compound | Solubility (% w/v) | Solution pH | Commencement of precipitation |
|---|---|---|---|
| ID | >50 | 7.5 | 24 h |
| IP | >20 | | |
| SD | 1.36 | 7.6 | |
| PD | practically insoluble | | |
| AD | practically insoluble | | |

The salt of diclofenac with a base of formula (I) also has high shelf-life. The pharmaceutical compositions according to the present invention contain a therapeutically active quantity of the salt of diclofenac with a base of formula (I) together with pharmaceutically acceptable liquid or solid excipients of organic or inorganic type, and can be administered orally. Preferably, said compositions contain an active ingredient quantity corresponding to 10-200 mg of diclofenac per unit dosage.

Examples of preferred pharmaceutical forms are granular forms packaged in sachets of water-impermeable material, and are dissolved in a little water to form solutions for oral administration.

In addition to the excipients, said compositions can contain preservatives, stabilizers, wetting agents, emulsifiers, osmotic pressure regulating salts, buffers, dyestuffs, sweeteners and flavorings. They are prepared by known methods and can contain other therapeutic agents.

The following examples are described by way of non-limiting illustration of the present invention.

EXAMPLE 1

Preparation of the salt of diclofenac with hydroxyethylpyrrolidine 14.75 g (49.8 mmoles) of 2-[(2,6-dichlorophenyl)-amino]benzeneacetic acid (diclofenac) were dissolved in acetone (50 ml), and 5.75 g (49.9 mmoles) of freshly distilled hydroxyethylpyrrolidine were added to the solution obtained.

After keeping the solution under agitation for one hour at ambient temperature, the solvent was removed under vacuum at 40° C.

The oily residue was treated with hexane (100 ml) and the obtained mixture kept under energetic agitation until the oil was transformed into a crystalline solid, which was separated by filtration and dried. 17 g of product were obtained having an M.P. of 57°–58° C. (yield 83% of theoretical).

The unrefined product obtained in this manner was dissolved in acetone (50 ml), decolorized with animal charcoal and filtered. The solution was evaporated under vacuum, and the residue treated with hexane as described heretofore. The salt of diclofenac with hydroxyethylpyrrolidine was obtained in its pure state, with an M.P. of 97.5°–100° C.

EXAMPLE 2

Preparation of the salt of Diclofenac with 1-(2-hydroxyethyl)-piperidine

A solution of 8.9 g of 2--/(2,6-dichloro-phenyl)-amino]-phenylactic acid in 220 ml of ethyl acetate is treated with a solution of 3.88 g of 1-(2-hydroxyethyl)-piperidine in 20 ml ethyl acetate while stirring.

After 30 minutes the clear solution is concentrated under reduced pressure to a volume of 100 ml and diluted with 100 ml diethyl ether. The crystalline 1-(2-hydroxyethyl)-piperidine salt of 2-[(2,6-dichlorophenyl)-amino]-phenylacetic acid precipitates and is filtered off. M.P. 109°–111°; solubility in water: 20% w/v.

EXAMPLE 3

Preparation of a granulate containing the salt of diclofenac with hydroxyethylpyrrolidine A granulate was prepared having the following composition:

| | |
|---|---|
| Salt of diclofenac with hydroxyethylmirrolydine | 70 mg |
| Sorbitol | 1798 mg |
| Aspartame | 50 mg |
| Polyethyleneglycol 6000 | 150 mg |
| E 124 | 1 mg |
| E 110 HC | 1 mg |
| Flavoring | 130 mg |

70 g of the salt of diclofenac with hydroxyethylpyrrolidine, 1.798 Kg of sorbitol and 50 g of aspartame were mixed together in a steel cube mixer for 20 minutes.

150 g of polyethyleneglycol 6000, 1 g of E 124 and 1 g of E 110 HC were dissolved in 280 ml of boiling water under agitation.

The solid mixture and solution prepared in this manner were mixed together in a fluidized bed granulator using 100 ml of mixing water. The granulate obtained in this manner was sieved through an oscillating screen with a mesh size of 1 mm.

130 g of flavoring was sieved separately with the same screen, and was mixed with the said granulate in a cube mixer for 20 minutes.

The granulate obtained in this manner was dispensed into sachets of water-impermeable material, dispensing 2,2 g of granulate into each sachet.

At the moment of use, the contents of each sachet were easily dissolved in a little water to form a drinkable solution which in terms of acid contains 50 mg of diclofenac.

We claim:

1. A water soluble salt, comprising:
   diclofenac (2-[(-2,6-dichlorophenyl)-amino-]benzeneacetic acid); and
   a cyclic organic base having the formula

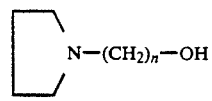

wherein n is 2.

2. A pharmaceutical composition comprising a therapeutically active quantity of a water soluble salt of diclofenac and a cyclic organic base having the formula

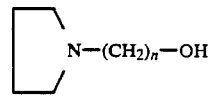

wherein n is 2, together with a pharmaceutically acceptable excipient.

3. The composition of claim 2, wherein a quantity of the salt of diclofenac and said cyclic organic base corresponding to 10–200 mg of diclofenac per unit dosage is present.

4. The composition of claim 2, wherein said composition is in granular form and is packaged in a water-impermeable sachet.

* * * * *

UNITED STATES PATENT AND TRADEMARK OFFICE
CERTIFICATE OF CORRECTION

PATENT NO. : 4,948,805

DATED : August 14, 1990

INVENTOR(S) : Antonio Ziggiotti and Michele DiSchiena

It is certified that error appears in the above-identified patent and that said Letters Patent is hereby corrected as shown below:

On the title page:
      Change the Assignee [73] from "Altergon S.A. & Ricerfarma Srl., Italy" to --Altergon S.A., Lugano, Switzerland--.

Signed and Sealed this

Seventh Day of January, 1992

Attest:

HARRY F. MANBECK, JR.

*Attesting Officer*      *Commissioner of Patents and Trademarks*